United States Patent
Sun et al.

(10) Patent No.: US 9,951,153 B2
(45) Date of Patent: Apr. 24, 2018

(54) METHOD OF MAKING AN OLEFIN POLYMERIZATION CATALYST ACTIVATOR

(71) Applicant: Dow Global Technologies LLC, Midland, MI (US)

(72) Inventors: Lixin Sun, Missouri City, TX (US); Daniel D. VanderLende, Sugar Land, TX (US)

(73) Assignee: Dow Global Technologies LLC, Midland, MI (US)

( * ) Notice: Subject to any disclaimer, the term of this patent is extended or adjusted under 35 U.S.C. 154(b) by 444 days.

(21) Appl. No.: 14/416,706

(22) PCT Filed: Jul. 31, 2013

(86) PCT No.: PCT/US2013/052827
§ 371 (c)(1),
(2) Date: Jan. 23, 2015

(87) PCT Pub. No.: WO2014/022461
PCT Pub. Date: Feb. 6, 2014

(65) Prior Publication Data
US 2015/0203602 A1 Jul. 23, 2015

Related U.S. Application Data

(60) Provisional application No. 61/677,594, filed on Jul. 31, 2012.

(51) Int. Cl.
| | |
|---|---|
| *C08F 4/54* | (2006.01) |
| *C07F 5/02* | (2006.01) |
| *C08F 4/52* | (2006.01) |
| *C08F 10/00* | (2006.01) |

(52) U.S. Cl.
CPC .............. *C08F 4/52* (2013.01); *C07F 5/027* (2013.01); *C08F 10/00* (2013.01)

(58) Field of Classification Search
None
See application file for complete search history.

(56) References Cited

U.S. PATENT DOCUMENTS

| | | | |
|---|---|---|---|
| 4,254,060 A | * | 3/1981 | Kimura .................... B01J 31/04 502/324 |
| 4,522,987 A | | 6/1985 | Hogan et al. |
| | | | (Continued) |

FOREIGN PATENT DOCUMENTS

| | | |
|---|---|---|
| WO | 1988002009 | 3/1988 |
| WO | 9730992 A1 | 8/1997 |
| | (Continued) | |

OTHER PUBLICATIONS

Chinese Second Office Action dated Oct. 10, 2016; from Chinese counterpart Application No. 201380051096.8.
(Continued)

*Primary Examiner* — Catherine S Branch
(74) *Attorney, Agent, or Firm* — Dinsmore & Shohl LLP

(57) ABSTRACT

A method for preparing ammonium tetrakis(pentafluorophenyl)borate salt comprising reacting a secondary amine with an aldehyde to form an iminium ion; hydrogenating the iminium ion by reaction with a reducing agent to form a tertiary amine; reacting the tertiary amine with a mineral acid to form an amine salt; and reacting the amine salt with $K[B(C_6F_5)_4]$, $Li[B(C_6F_5)_4]$, or combinations thereof to form an ammonium tetrakis(pentafluorophenyl)borate salt, wherein the secondary amine is derived from a non-animal source and the aldehyde has seven or more carbon atoms; wherein the ammonium tetrakis(pentafluorophenyl)borate salt is characterized by a solubility at 25° C. in hexane, cyclohexane or methylcyclohexane of at least 10 weight percent; and wherein the tertiary amine has a molecular weight of at least 450 g/mole is provided.

11 Claims, 3 Drawing Sheets

(56) References Cited

U.S. PATENT DOCUMENTS

| | | | |
|---|---|---|---|
| 4,543,399 A | 9/1985 | Jenkins, III et al. |
| 4,564,647 A | 1/1986 | Hayashi et al. |
| 4,588,790 A | 5/1986 | Jenkins, III et al. |
| 5,032,652 A | 7/1991 | Chang |
| 5,084,534 A | 1/1992 | Welborn, Jr. et al. |
| 5,132,380 A | 7/1992 | Stevens et al. |
| 5,153,157 A | 10/1992 | Hlatky et al. |
| 5,198,401 A | 3/1993 | Turner et al. |
| 5,405,922 A | 4/1995 | DeChellis et al. |
| 5,470,927 A | 11/1995 | Turner et al. |
| 5,919,983 A * | 7/1999 | Rosen | C07F 5/027 502/152 |
| 6,011,029 A | 1/2000 | Ding et al. |
| 6,949,642 B2 | 9/2005 | Gao et al. |
| 2002/0169313 A1 | 11/2002 | Gao et al. |
| 2015/0203602 A1 | 7/2015 | Sun et al. |

FOREIGN PATENT DOCUMENTS

| WO | 1997035893 | 10/1997 |
|---|---|---|
| WO | WO09735893 | 10/1997 |
| WO | WO2010/010017 | 1/2010 |

OTHER PUBLICATIONS

Hiroshi Kimura et al., Catalysis Letters vol. 99, Nos. 3-4, Feb. 2005, p. 119-131, 13 pages.
PCT/US2013/052827 International Search Report and Written Opinion dated Sep. 30, 2013, 9 pages.
PCT/US2013/052827 International Preliminary Report on Patentability dated Oct. 23, 2014, 15 pages.
EPO Rules 161(1) and 162 Communication for counterpart EP Application No. 13748417.6 dated Mar. 6, 2015, 2 pages.
Japanese Office Action dated Jan. 3, 2017; from counterpart India Application No. 2015-525531.
EP Response to Office Action dated Sep. 15, 2015; from EP counterpart Application No. 13748417.6.
Frederick A. Bettelheim, Introduction to General, Organic and Biochemistry, 11th Edition By , William H. Brown, Mary K. Campbell, Shawn O. Farrell, Omar Torres, p. 114, 2013, (Boston).
Eric Block, Nomenclature of Amines, www.Britannica.com, as down loaded, Nov. 20, 2017.

* cited by examiner

METHOD OF MAKING AN OLEFIN POLYMERIZATION CATALYST ACTIVATOR

FIELD OF INVENTION

The instant invention relates to a method for making a catalyst activator, a catalyst composition containing the activator, and a polymerization method utilizing such catalyst composition.

BACKGROUND OF THE INVENTION

Catalyst activators for use in polymerization of α-olefins are advantageous for use in a continuous solution polymerization process wherein catalyst, catalyst activator, and at least one polymerizable monomer are continuously added to a reactor operating under solution polymerization conditions, and polymerized product is continuously removed therefrom.

It is previously known in the art to activate single site or homogeneous (e.g., Ziegler-Natta) polymerization catalysts by the use of Bronsted acid salts capable of transferring a proton to form a cationic derivative of such Group 4 metal complex. Preferred Bronsted acid salts are such compounds containing a non-coordinating anion that is capable of stabilizing the resulting Group 4 metal cation, especially tetrakis(pentafluorophenyl)borate. Examples of such Bronsted acid salt activators, which are a species of ionic activator, are protonated ammonium, sulfonium, or phosphonium salts disclosed in, for example, U.S. Pat. Nos. 5,198,401, 5,132,380, 5,470,927, and 5,153,157.

Due to the fact that such activators are fully ionized, and the corresponding anion is highly non-coordinating, such activators are extremely effective as olefin polymerization catalyst activators. Disadvantageously, however, because they are ionic salts, such activators are extremely insoluble in aliphatic hydrocarbons, and only sparingly soluble in aromatic solvents. It is desirable to conduct most polymerizations of α-olefins in aliphatic hydrocarbon solvents due to the compatibility of such solvents with the monomer and in order to reduce the aromatic hydrocarbon content of the resulting polymer product. Normally, ionic salt activators need to be added to such polymerizations in the form of a solution in an aromatic solvent such as toluene. The use of even a small quantity of such an aromatic solvent for this purpose is undesirable since it must be removed in a devolatilization step and separated from other volatile components, a process that adds significant cost and complexity to any commercial process. In addition, the foregoing ionic cocatalysts often exist in the form of an oily, intractable material which is not readily handled and metered or precisely incorporated into the reaction mixture.

Highly soluble ammonium tetrakis(pentafluorophenyl) borate catalyst activator has been developed and successfully used in polyolefin production. Such activator is described in PCT Publication No. WO1997035893. Such highly soluble catalyst activator comprised a bis(hydrogenated tallowalkyl)methylamine derived from beef tallow. Due to increasing concerns over animal-derived material, and possible spread of Transmissible Spongiform Encephalopathies, there is a need to develop a highly soluble borate activator produced exclusively from non-animal-derived material. However, non-animal-derived high molecular weight tertiary amines that can be used as a direct replacement for the tertiary amine derived from beef tallow, currently, is not commercially available. Therefore, a method of making a tertiary amine for use in producing highly soluble catalyst activator, wherein the process does not utilize animal-derived products, is desirable.

SUMMARY OF THE INVENTION

The instant invention is a method of making a catalyst activator, a catalyst composition containing the activator, and a polymerization method utilizing such catalyst composition.

In one embodiment, the instant invention provides for preparing ammonium tetrakis(pentafluorophenyl)borate salt comprising: reacting a secondary amine with an aldehyde to form an iminium ion; hydrogenating the iminium ion by reaction with a reducing agent to form a tertiary amine; reacting the tertiary amine with HCl to form a amine chlorine salt; and reacting the amine chlorine salt with $K[B(C_6F_5)_4]$ to form an ammonium tetrakis(pentafluorophenyl)borate salt, wherein the secondary amine is derived from a non-animal source and the aldehyde has seven or more carbon atoms; wherein the ammonium tetrakis(pentafluorophenyl)borate salt is characterized by a solubility at 25° C. in hexane, cyclohexane or methylcyclohexane of at least 20 weight percent; and wherein the tertiary amine has a molecular weight of at least 450 g/mole.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

DETAILED DESCRIPTION OF THE INVENTION

Figure 1:
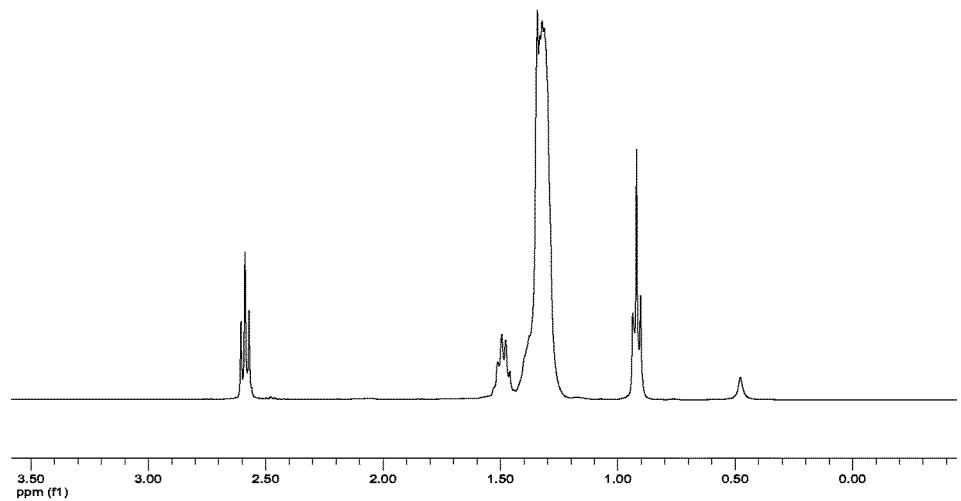
FIG. 1 is an $H^1$-NMR spectrum of ARMEEN 2C.

The instant invention is a method for preparing a catalyst activator, namely ammonium tetrakis(pentafluorophenyl) borate salt, a catalyst composition containing the activator, and a polymerization method utilizing such catalyst composition.

As used herein, the term highly soluble refers to solubility in aliphatic solvents, including condensed α-olefin monomers.

As used herein, non-animal-derived means not produced from any animal body components, including for example, beef tallow. Non-animal-derived products includes, by way of example, products derived from plant sources and/or gas and/or petroleum from geologic formations.

The method for preparing ammonium tetrakis(pentafluorophenyl)borate salt according to the present invention comprises: reacting a secondary amine with an aldehyde to form an iminium ion; hydrogenating the iminium ion by reaction with a reducing agent to form a tertiary amine; reacting the tertiary amine with HCl to form an amine chlorine salt; and reacting the amine chlorine salt with K[B(C$_6$F$_5$)$_4$] to form an ammonium tetrakis(pentafluorophenyl)borate salt, wherein the secondary amine is derived from a non-animal source and the aldehyde has seven or more carbon atoms; wherein the ammonium tetrakis(pentafluorophenyl)borate salt is characterized by a solubility at 25° C. in hexane, cyclohexane or methylcyclohexane of at least 20 weight percent; and wherein the tertiary amine has a molecular weight of at least 450 g/mole.

Secondary amines useful in embodiments of the invention include any secondary amine which is non-animal-derived. In certain embodiments, the secondary amine are selected from the group consisting of dialkylamines, having the formula R$_3$R$_4$NH, wherein R$_3$ and R$_4$ can be the same or different groups and wherein each of R$_3$ and R$_4$ are selected from the group consisting of linear aliphatics, branched aliphatics. In certain embodiments, the aliphatics comprise from 1 to 30 carbon atoms. All individual values and subranges from 1 to 30 carbon atoms are included herein and disclosed herein; for example, the number of carbon atoms in each of R$_3$ and R$_4$ may be from a lower limit of 1, 3, 5, 7, 9, 11, 13, 15, 17 19, 21, 23. 25, 27 or 29 to an upper limit of 2, 4, 6, 8, 10, 12, 14, 16, 18, 20, 22, 24, 26 or 30. For example, the number of carbon atoms in each of R$_3$ and R$_4$ may be in the range from 1 to 30, or in the alternative, from 5 to 25, or in the alternative, from 10 to 20, or in the alternative from 2 to 16, or in the alternative, from 15 to 30. In some embodiments, the number of carbons atoms in R$_3$ and R$_4$, combined, may be in the range from 8 to 60. All individual values and subranges from 8 to 60 carbon atoms are included herein and disclosed herein; for example the total carbons in R$_3$ and R$_4$ may be from a lower limit of 8, 20, 30, 40, or 50 to an upper limit of 9, 19, 29, 38, 47, 55, or 60. For example, the combined number of carbon atoms in R$_3$ and R$_4$ may be in the range of from 8 to 60, or in the alternative, from 15 to 50, or in the alternative, from 22 to 38. the secondary amines comprise linear and/or branched aliphatic groups.

In particular embodiments, the secondary amine is selected from the group consisting of dicocoalkylamines, wherein the alkyl groups have from 8 to 22 carbon atoms. All individual values and subranges from 8 to 22 carbon atoms are included herein and disclosed herein; for example, the number of carbon atoms in the alkyl group may be from a lower limit of 8, 10, 12, 14, 16, 18, or 20 carbon atoms to an upper limit of 2, 11, 13, 15, 17, 19, 21 or 22 carbon atoms. The number of carbon atoms in the alkyl group may be in the range from 8 to 22 carbon atoms, or in the alternative, from 10 to 18 carbon atoms, or in the alternative, from 8 to 15 carbon atoms, or in the alternative from 14 to 22 carbon atoms, or in the alternative from 11 to 16 carbon atoms, or in the alternative from 12 to 14 carbon atoms. In an alternative embodiment, the secondary amine is selected from the group consisting of di-octadecylamine, di-cocoamine, methylbenzylamine, and combinations thereof.

Aldehydes useful in embodiments of the invention include any aldehyde having seven or more carbon atoms. All individual values of seven or greater carbon atoms are disclosed herein and included herein; for example, the number of carbon atoms in the aldehydes useful in forming the catalyst activator may be from a lower limit of 7, 8, 9, 10, 11, 12, or 13 carbon atoms. Exemplary aldehydes include heptaldehyde, octaldehyde, nonaldehyde, decaldehyde, dodecyladehyde, and combinations thereof.

The reaction between the secondary amine and the aldehyde forms an iminium ion and water and the reaction is reversible. In some embodiments of the invention, the reaction is driven to completion by conditions which remove the water from the iminium ion/water product mixture. Such conditions may include appropriate temperatures and/or pressures. In alternative embodiments, the reaction between aldehyde and secondary amine occurs in the presence of a dehydrating agent. Any dehydrating agent which is inert to the unreacted aldehyde and secondary amine and product imminium ion may be used. Exemplary dehydrating agents include MgSO$_4$, Na$_2$SO$_4$, CaCl$_2$, molecular sieves, activated alumina, silica gel, and combinations of two or more thereof. The reaction to form the imminium ion may be depicted as follows:

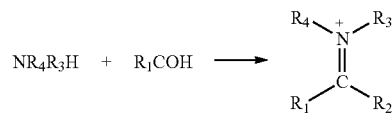

NR$_4$R$_3$H + R$_1$COH ⟶ wherein R$_4$ and R$_3$ are described above, R$_2$ is a hydrogen, and R$_1$ is an alkyl having seven or more carbon atoms.

The reaction between the secondary amine and the aldehyde may take place in a solvent in which both the amine and aldehyde are soluble. Suitable solvents include, for example, tetrahydrofuran (THF), 1,2-dichloroethane (DCE), acetonitrile and combinations thereof.

The imminium ion is then reacted with a reducing agent to form the tertiary amine. Any reducing agent capable of donating a hydrogen so as to form the tertiary amine may be used. Exemplary reducing agents include sodium triacetoxyborohydride. NaBH$_4$, NaBH$_3$CN, Zn(BH$_4$)$_2$, ((C$_6$H$_5$)$_3$P)$_2$Cu (BH$_4$), NR$_4$BH$_4$, BH$_3$, and combinations of two or more thereof.

The tertiary amine has a molecular weight of at least 450 g/mole. All individual values of 450 and greater g/mole are included herein and disclosed herein. For example, the tertiary amine may have a molecular weight of at least 450, 475, 500, 525, 550, or 575 g/mole. In an alternative embodiment, the instant invention provides a method for preparing ammonium tetrakis(pentafluorophenyl)borate salt in accordance with any of the preceding embodiments, except that the tertiary amine has a molecular weight from 450 to 5000 g/mole, or in the alternative, from 450 to 1000 g/mole, or in the alternative, from 450 to 800 g/mole, or in the alternative, from 450 to 600 g/mole, or in the alternative, from 550 to 1500 g/mole, or in the alternative, from 500 to 3000 g/mole.

The tertiary amine(s) formed by hydrogenation of the imminium ion is then reacted one or more mineral acids, such as HCl and HBr to form an amine chlorine salt. The amine chloride salt is then reacted with K[B(C$_6$F$_5$)$_4$], Li[B(C$_6$F$_5$)$_4$], or combinations thereof to form an ammonium tetrakis(pentafluorophenyl)borate salt.

In an alternative embodiment, the instant invention provides a method for preparing ammonium tetrakis(pentafluorophenyl)borate salt in accordance with any of the preceding embodiments, except that the ammonium tetrakis(pentafluorophenyl)borate salt is produced at a level of at least 80% based on amount of potassium tetrakis(pentafluorophenyl)borate. All individual values from at least 80% are included herein and disclosed herein. For example, the minimum conversion of the potassium tetrakis(pentafluorophenyl)borate into ammonium tetrakis(pentafluorophenyl)borate salt may be from a lower limit of 80, 82, 84, or 86%.

In an alternative embodiment, the instant invention provides a method for preparing ammonium tetrakis(pentafluorophenyl)borate salt in accordance with any of the preceding embodiments, except that the ammonium tetrakis(pentafluorophenyl)borate salt is selected from the group consisting of cyclohexyldi(dodecyl)ammonium tetrakis(pentafluorophenyl)borate, di(octadecyl)methylammonium tetrakis(pentafluorophenyl)borate, di(octadecyl)(n-butyl)ammonium tetrakis(pentafluorophenyl)borate, di(docosyl)methylammonium tetrakis(pentafluorophenyl)borate, and combinations thereof.

In an alternative embodiment, the instant invention provides a method for preparing ammonium tetrakis(pentafluorophenyl)borate salt in accordance with any of the preceding embodiments, except that the ammonium tetrakis(pentafluorophenyl)borate salt is soluble in methylcyclohexane at levels greater than 10 wt %. All individual values from greater than 10 wt % are included herein and disclosed herein. For example, the solubility of the ammonium tetrakis(pentafluorophenyl)borate salt in methylcyclohexane may be greater than 10, or in the alternative, greater than 25, or in the alternative, greater than 29, or in the alternative, greater than 31 wt % based on the total weight of the ammonium tetrakis(pentafluorophenyl)borate salt and the methylcyclohexane (MCH).

In an alternative embodiment, the instant invention provides a catalyst composition comprising the ammonium tetrakis(pentafluorophenyl)borate salt made in accordance with any of the preceding embodiments of the inventive method.

In yet another embodiment, the instant invention provides a polymerization process comprising contacting one or more α-olefins under polymerization conditions with a catalyst composition of any of the preceding embodiments.

In general, the polymerization may be accomplished at conditions well known in the prior art for heterogeneous (i.e. Ziegler-Natta) or homogeneous (i.e. single site; Kaminsky-Sinn) type polymerization reactions. Suspension, solution, slurry, gas phase or high pressure, whether employed in batch or continuous form or other process conditions, may be employed if desired. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere. Preferred polymerization temperatures are from 0-250.degree. C. Preferred polymerization pressures are from atmospheric to 3000 atmospheres.

However, the advantages of the invention are particularly noticed when the present catalyst system is used in a solution polymerization, more preferably a continuous solution polymerization process, in the presence of an aliphatic or alicyclic liquid diluent. By the term "continuous polymerization" is meant that at least the products of the polymerization are continuously removed from the reaction mixture, such as for example by devolatilization of a portion of the reaction mixture. Preferably one or more reactants are also continuously added to the polymerization mixture during the polymerization. Examples of suitable aliphatic or alicyclic liquid diluents include straight and branched-chain hydrocarbons such as isobutane, butane, pentane, hexane, heptane, octane, and mixtures thereof; alicyclic hydrocarbons such as cyclohexane, cycloheptane, methylcyclohexane, methylcycloheptane, and mixtures thereof; and perfluorinated hydrocarbons such as perfluorinated $C_{4-10}$ alkanes, and the like. Suitable diluents also include aromatic hydrocarbons (particularly for use with aromatic α-olefins such as styrene or ring alkyl-substituted styrenes) including toluene, ethylbenzene or xylene, as well as liquid olefins (which may act as monomers or comonomers) including ethylene, propylene, butadiene, cyclopentene, 1-hexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable.

EXAMPLES

The following examples illustrate the present invention but are not intended to limit the scope of the invention.

Preparation of Inventive Example 1

Preparation of Heptylated Secondary Amine: 2 g of ARMEEN 2C (5.13 mmol) was dissolved in 30 ml of tetrahydrofuran (THF) in a 100 ml flask purged with nitrogen. 0.72 ml of heptaldehyde (5.13 mmol) was added to the flask. $MgSO_4$ in an amount sufficient to drive the reaction to completion by absorption of byproduct water was also added to the flask. The mixture was heated to 60° C. and stirred for 6 hours. The mixture was then filtered and the filtrate was placed in a clean flask under nitrogen. 1.68 g of $NaBH(OAc)_3$ (8.0 mmol) was added and the mixture was stirred at room temperature for 40 hours. The mixture was then quenched by 3N aqueous NaOH. The product was extracted by ether extraction twice. The organic phase was dried over $MgSO_4$. The dried organic phase was then filtered. The solvent was then removed from the organic phase by rotovaporation thereby obtaining heptylated ARMEEN 2C. ARMEEN 2C is dicocoalkylamine, wherein the alkyl groups have from between about 12 and about 14 carbon atoms, which is commercially available from Akzo Nobel Surface Chemistry LLC (Chicago, Ill., USA)

Preparation of Ammonium Borate Salt: 1.5 g of heptylated ARMEEN 2C (3.08 mmol) was dissolved in 30 ml of methylcyclohexane (MCH) in a 2 ounce jar. 3.08 mmol of aqueous 1 N HCl was added to the jar by syringe and stirred for 45 min. 2.212 g of potassium tetrakis(pentafluorophenyl) borate (3.08 mmol) and 20 ml of water were then added to the jar. This mixture was then stirred at room temperature (about 21° C.) for 2 hrs. The mixture was then transferred to a separatory funnel and extracted with saturated aqueous NaCl twice. The organic phase was then placed in rotovap to remove the solvent. 3.2 g of yellowish viscous oil was recovered. 1 g of the yellowish viscous oil was removed for solubility testing. The remaining part of the yellowish viscous oil was dissolved in 40 ml of toluene, dried with $MgSO_4$ overnight, filtered, transferred to a bottle and sparged with nitrogen thoroughly and finally placed in a drybox. The concentration was then measured by gravimetric method to be 5.94 wt % (0.044 mmol/ml).

Figure 2:
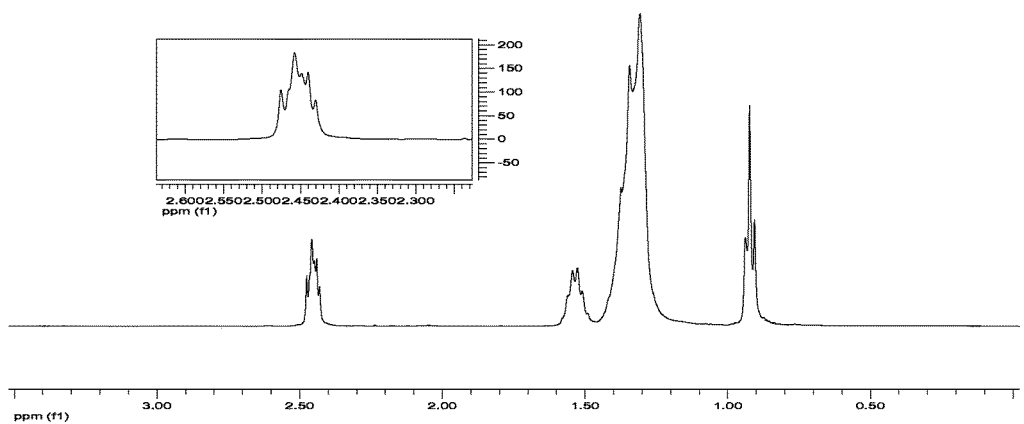
FIG. 2 is an $H^1$-NMR spectrum of heptylated ARMEEN 2C made in connection with Inventive Example 1.

The same procedure was used to prepare Comparative Examples 1 and 2 and Inventive Example 2, using different aldehydes, as shown in Table 1. FIG. 1 illustrates first the H1-NMR spectrum of ARMEEN 2C. FIG. 2 illustrates the H1-NMR spectrum of the heptylated ARMEEN 2C. These spectra show a clear shift of α-$CH_2$ peaks from around 2.6 ppm to 2.42-2.5 ppm, indicating successful alkylation of the ARMEEN 2C.

TABLE 1

|  | Aldehyde (CH$_2$R') | Yield of Alkylated Secondary Amine (ARMEEN 2C) (R$_2$NCH$_2$R') Yield, % | Borate complex Yield, % | % Solubility in MCH |
|---|---|---|---|---|
| Comparative Example 1 | Formaldehyde | 87.9 | 77.2 | 3.02 |
| Comparative Example 2 | Butylaldehyde | 96.4 | 79.1 | 1.25 |
| Inventive Example 1 | Heptylaldehyde | 97.5 | 88.9 | >27 |
| Inventive Example 2 | Dodecylaldehyde | 84.9 | 86.2 | >27 |

Alternative, comparative, alkylation methods were also examined.

Comparative Alkylation Method 1: 5 g of ARMEEN 2C (12.83 mmol) was dissolved in 100 ml of THF in a 250 ml flask purged with nitrogen. 1.38 ml of 1-bromobutane (12.83 mmol) was added dropwise. The mixture was stirred at room temperature for 24 hours. The mixture was then washed with distilled water and the organic phase isolated. The solvent was removed from the organic phase by rotovaporation.

Figure 3:
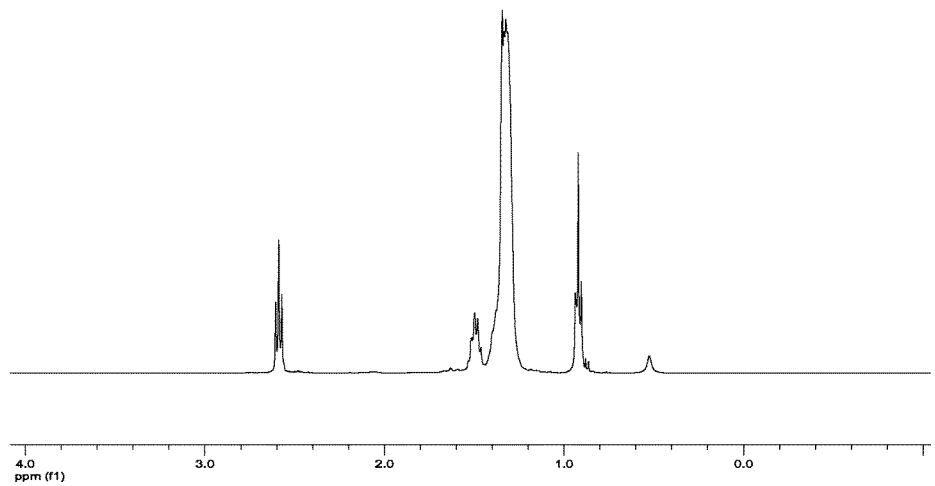
FIG. 3 is an $H^1$-NMR spectrum of ARMEEN 2C treated with 1-bromobutane (Comparative alkylation method 1)

FIG. 3 illustrates the H1-NMR of the resultant organic phase showed no change or shift of the α-CH$_2$ peaks, indicating unsuccessful reaction.

Comparative Alkylation Method 2: 2.0 g of ARMEEN 2C (5.13 mmol) was dissolved in 50 ml of THF in a 100 ml round bottom flask under nitrogen. 1.34 ml of N,N-diisopropylethylamine (Hunig base) (7.70 mmol) and 0.61 ml of 1-bromobutane (5.64 mmol) were added and stirred at room temperature (about 21° C.) for 24 hours. The reaction mixture was washed by saturated aqueous NaCl. The organic phase was dried over MgSO$_4$, filtered, and evaporated to dryness by rotovap.

Figure 4:
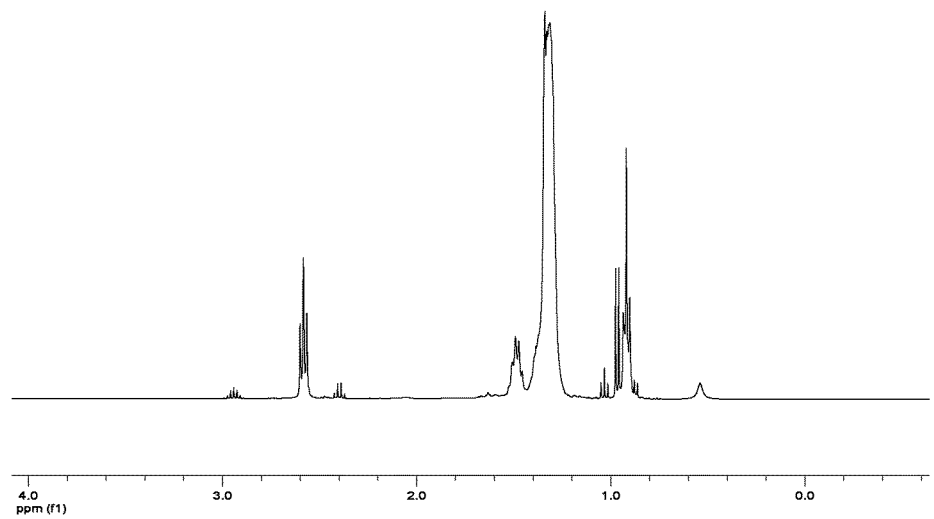
FIG. 4 is an $H^1$-NMR spectrum of ARMEEN 2C treated with 1-bromobutane in the presence of Hunig Base (Comparative alkylation method 2)

FIG. 4 illustrates the H1-NMR spectrum of the product organic phase showing no change or shift of the α-CH2, thus indicating unsuccessful reaction.

Comparative Alkylation Method 3: 0.762 g of didecylamine (2.56 mmol) was dissolved in 10 ml of 1,4-dioxane under nitrogen atmosphere. A catalytic amount of IrCl3 (about 4 mg) was added, followed by 0.23 ml of butyraldehyde (2.56 mmol) and 0.31 ml of polymethylhydrosiloxane (PMHS). The mixture was stirred at 75° C. for 5 hours. The mixture was then quenched with excessive amount of wet ether, and extracted two times with ether and water. The organic phase was dried over MgSO$_4$, filtered and evaporated to dryness by rotovap.

Figure 5:
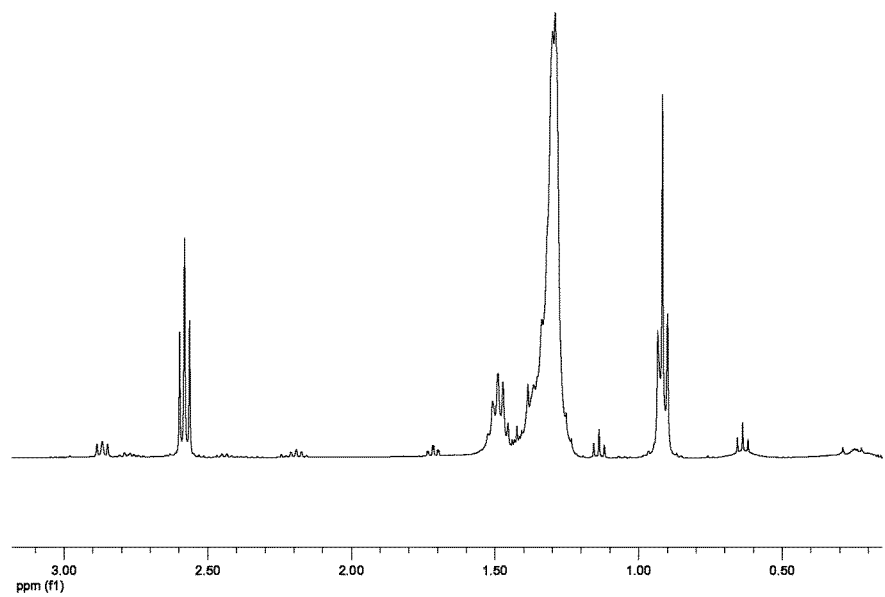
FIG. 5 is an $H^1$-NMR spectrum of ARMEEN 2C treated by catalytic alkylation by iridium catalyst (Comparative alkylation method 3)

FIG. 5 illustrates the H1-NMR spectrum of the product, which indicates no change or shift of the alpha-CH2 peaks, indicating unsuccessful reaction.

Comparative Alkylation Method 4: 2 g of ARMEEN 2C (5.13 mmol) was dissolved in 30 ml of THF in a 100 ml flask purged with nitrogen. 0.72 ml of heptaldehyde (5.13 mmol) and an amount of MgSO$_4$ sufficient to drive the reaction to completion were added to the flask. The mixture was heated to 60° C. and stirred for 6 hours. The mixture was then filtered and the filtrate was placed in a clean flask under nitrogen. 1.68 g of NaBH(OAc)$_3$ (8.0 mmol) was added and the mixture was stirred at room temperature (about 21° C.) for 40 hours. The mixture was then quenched by 3N aqueous NaOH. The product organic phase was extracted by ether twice. The organic phase was dried over MgSO$_4$, and filtered. The solvent was then removed by rotovaporation.

Figure 6:
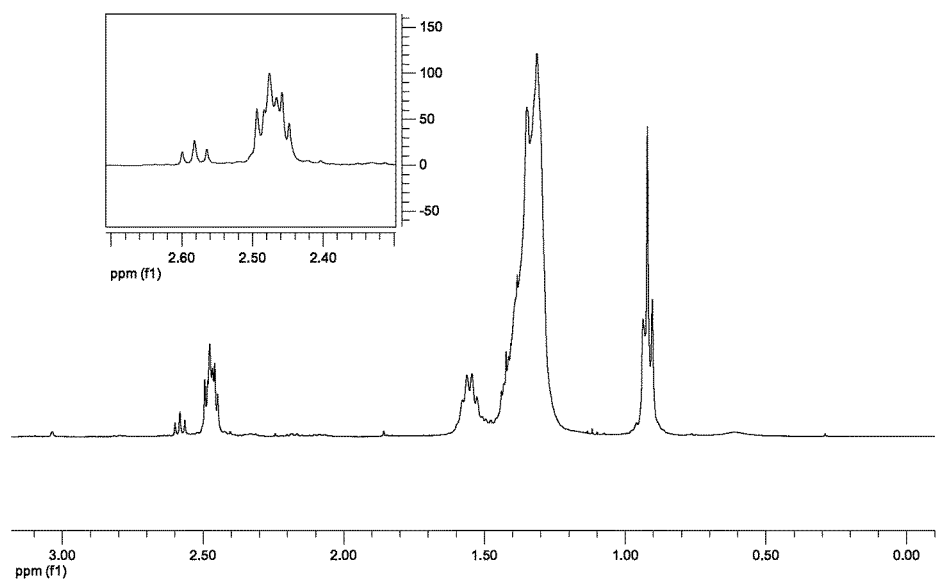
FIG. 6 is an $H^1$-NMR spectrum of ARMEEN 2C treated by reductive alkylation without a dehydrating agent (Comparative alkylation method 4).

FIG. 6 illustrates the H1-NMR spectrum of the product organic phase, which shows new peaks at 2.42-2.50 ppm and smaller peaks at around 2.6 ppm. The presence of the latter peaks indicated incomplete reaction.

The present invention may be embodied in other forms without departing from the spirit and the essential attributes thereof, and, accordingly, reference should be made to the appended claims, rather than to the foregoing specification, as indicating the scope of the invention.

We claim:

1. A method for preparing ammonium tetrakis(pentafluorophenyl)borate salt comprising:
   reacting a secondary amine with an aldehyde to form an iminium ion;
   hydrogenating the iminium ion by reaction with a reducing agent to form a tertiary amine; reacting the tertiary amine with mineral acid to form an amine salt; and
   reacting the amine salt with K[B(C$_6$F$_5$)$_4$], Li[B(C$_6$F$_5$)$_4$], or a combination thereof, to form an ammonium tetrakis(pentafluorophenyl)borate salt,
   wherein the secondary amine is derived from a non-animal source and the aldehyde has seven or more carbon atoms;
   wherein the ammonium tetrakis(pentafluorophenyl)borate salt is characterized by a solubility at 25° C. in hexane, cyclohexane or methylcyclohexane of at least 10 weight percent; and
   wherein the tertiary amine has a molecular weight of at least 450 g/mole.

2. The method according to claim 1, wherein the reacting a secondary amine with an aldehyde occurs under conditions to drive the reaction to completion.

3. The method according to claim 2, wherein the reacting a secondary amine with an aldehyde occurs in the presence of a dehydrating agent selected from the group consisting of MgSO$_4$, Na$_2$SO$_4$, CaCl$_2$, molecular sieves, activated alumina, silica gel, and combinations thereof.

4. The method according to claim 1, wherein the reducing agent is selected from the group consisting of sodium triacetoxyborohydride. NaBH$_4$, NaBH$_3$CN, Zn(BH$_4$)2, ((C$_6$H$_5$)$_3$P)$_2$Cu(BH$_4$), NR$_4$BH$_4$, BH$_3$, and combinations thereof.

5. The method according to claim 1, wherein the reducing agent is sodium triacetoxyborohydride.

6. The method according to claim 1, wherein the aldehyde is C$_7$H$_{14}$O.

7. The method according to claim 1, wherein the aldehyde is C$_{12}$H$_{24}$O.

8. The method according to claim 6, wherein the reacting the amine salt with K[B(C$_6$F$_5$)$_4$], Li[B(C$_6$F$_5$)$_4$], or a combination thereof to form the ammonium tetrakis(pentafluorophenyl)borate salt has at least an 80% yield based on the weight of potassium tetrakis(pentafluorophenyl)borate (K[B(C$_6$F$_5$)$_4$]).

9. The method according to claim 7, wherein the reacting the amine salt with K[B(C$_6$F$_5$)$_4$], Li[B(C$_6$F$_5$)$_4$], or a combination thereof to form the ammonium tetrakis(pentafluorophenyl)borate salt has at least an 80% yield based on the weight of potassium tetrakis(pentafluorophenyl)borate (K[B(C$_6$F$_5$)$_4$]).

10. The method according to claim 6, wherein the ammonium tetrakis(pentafluorophenyl)borate salt is soluble in methylcyclohexane at levels greater than 25 wt %.

11. The method according to claim 7, wherein the ammonium tetrakis(pentafluorophenyl)borate salt is soluble in methylcyclohexane at levels greater than 25 wt %.

* * * * *

UNITED STATES PATENT AND TRADEMARK OFFICE
CERTIFICATE OF CORRECTION

PATENT NO. : 9,951,153 B2
APPLICATION NO. : 14/416706
DATED : April 24, 2018
INVENTOR(S) : Lixin Sun and Daniel D. VanderLende Page 1 of 1

It is certified that error appears in the above-identified patent and that said Letters Patent is hereby corrected as shown below:

In the Claims

Column 8, Line 45, Claim 6:
"is $C_7H_14O$."
Should read:
--is $C_7H_{14}O$.--; and Column 8, Line 47, Claim 7:
"is $C_{12}H_24O$."
Should read:
--is $C_{12}H_{24}O$.--.

Signed and Sealed this
Eleventh Day of December, 2018

Andrei Iancu
*Director of the United States Patent and Trademark Office*